United States Patent

Boiteux et al.

[11] Patent Number: 5,681,938
[45] Date of Patent: Oct. 28, 1997

[54] METHOD FOR PREPARING SLIGHTLY COLORED ALKYLPOLYSACCHARIDES HAVING A LOW ACID BREAKDOWN PRODUCT CONTENT

[75] Inventors: Jean-Pierre Boiteux, Saix; Hervé Rolland, Castres, both of France

[73] Assignee: Societe D'Exploitation de Produits pour les Industries Chimiques-Seppic, Paris, France

[21] Appl. No.: 513,843

[22] PCT Filed: Mar. 10, 1994

[86] PCT No.: PCT/FR94/00263

§ 371 Date: Sep. 11, 1995

§ 102(e) Date: Sep. 11, 1995

[87] PCT Pub. No.: WO94/20513

PCT Pub. Date: Sep. 15, 1994

[30] Foreign Application Priority Data

Mar. 12, 1993 [FR] France ................................. 93 02877

[51] Int. Cl.$^6$ .................................................. C07H 1/00
[52] U.S. Cl. ........................ 536/18.6; 536/4.1; 536/18.5; 536/124
[58] Field of Search .......................... 536/4.1, 18.5, 536/18.6, 124

[56] References Cited

U.S. PATENT DOCUMENTS 4,939,245  7/1990  Rascle et al. .......................... 536/18.5

Primary Examiner—Elli Peselev
Attorney, Agent, or Firm—Dennison, Meserole, Pollack & Scheiner

[57] ABSTRACT

A process for the preparation of an alkylpolyoside containing from 6 to 32 carbon atoms in its alkyl chain, by the steps of:

a) reacting, in the presence of an acid catalyst, a saccharide or a source of saccharide with a fatty alcohol having a hydrocarbon chain containing at least 6 carbon atoms, or a lower alcohol of the formula $C_nH_{2n+1}OH$, in which n is an integer between 1 and 5, and a fatty alcohol having a hydrocarbon chain containing at least 6 carbon atoms;

b) neutralizing the catalyst used in step a); and c) removing excess fatty alcohol. The neutralizing takes place using a neutralizing agent which is a tertiary amine of the formulae

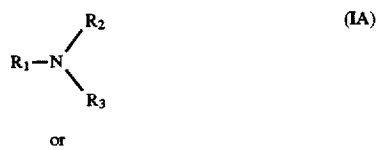

(IA)

or

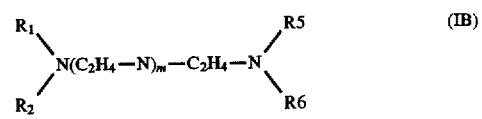

(IB)

in which:

—m is an integer between 0 and 5; and $R_1$, $R_2$, $R_3$, $R_4$, $R_5$ and $R_6$, which are identical or different, are independently:

an alkyl radical having from 1 to 6 carbon atoms, a hydroxyalkyl or dihydroxyalkyl radical having from 2 to 4 carbon atoms, a phenyl radical, or a radical of the formula $(C_nH_{2n}—O)_xH$, in which n is an integer between 2 and 4 and x is an integer between 2 and 5. $R_1R_2$ may be taken together with the nitrogen atom to which they are attached to be a saturated or unsaturated, substituted or unsubstituted heterocycle having from 5 to 7 ring members and containing from 1 to 3 heteroatoms selected from oxygen, nitrogen and sulfur.

8 Claims, No Drawings

METHOD FOR PREPARING SLIGHTLY COLORED ALKYLPOLYSACCHARIDES HAVING A LOW ACID BREAKDOWN PRODUCT CONTENT

BACKGROUND OF THE INVENTION

The present invention relates essentially to a novel process for the preparation of weakly colored alkylpolyosides having a low content of acid degradation products, obtained by reaction of a saccharide with an excess of a fatty alcohol in the presence of an acid catalyst, followed by neutralization with a base.

Alkylpolyosides are non-ionic surfactants which are already used in a wide range of industrial applications.

The preparation of alkylpolyosides from a reducing sugar and a fatty alcohol has been amply described in the literature.

The most commonly used processes involve the reaction of a monosaccharide (or a source of monosaccharide) with a fatty alcohol in the presence of an acid catalyst.

A variant of these processes consists in performing a transetherification, i.e. introducing a low-molecular alcohol, for example methanol or butanol, before or at the same time as the fatty alcohol, to give a short-chain alkylpolyoside, which reacts with the fatty alcohol to give a long-chain alkylpolyoside.

In all cases the reaction is carried out with a molar excess of fatty alcohol (generally 2 to 8 mol of fatty alcohol per monosaccharide unit), so it is subsequently necessary to remove the excess alcohol.

The excess fatty alcohol is generally removed by vacuum distillation.

However, as the alcohols used have high boiling points (of the order of 120° C. to 220° C. under residual pressures of between 0.5 and 20 mm of mercury), the distillation has to be carried out at a relatively high temperature, which can lead to problems regarding the color of the products obtained.

To limit the risks of coloration when the alcohol is removed, the currently most satisfactory industrial method consists in employing a falling film or rotating film evaporator or a flash evaporator. This technique, the main advantage of which is to reduce the product overheating times, has been described for example in the documents U.S. Pat. No. 3,565,885 and EP 0418458.

During the alcohol removal phase, the pH of the reaction medium is another parameter, apart from the temperature, which influences the final coloration of the products.

Before distillation of the alcohol, it is essential to neutralize the catalyst residues present in the reaction product. This neutralization must be effected within an optimum pH range. Thus an alkaline pH favors the degradation of the residual sugars present in the reaction medium with, in particular, the formation of very highly colored aldolic polycondensation products, whereas distillation at an excessively acid pH, albeit beneficial in terms of coloration, detracts from the stability of the alkylpolyosides to hydrolysis. In an acid medium, glucose, whether residual or formed by hydrolysis, is dehydrated to 5-hydroxymethylfurfural, which can degrade to give acids like formic acid or levulinic acid. Traces of acetic, lactic or glycolic acid are also found in certain commercial alkylpolyosides.

The catalyst is generally neutralized with a strong mineral base such as sodium or potassium hydroxide, which, given the anhydrous nature of the medium, makes pH adjustment more difficult.

Various neutralizing agents have been proposed in order to overcome these disadvantages.

The following may thus be mentioned:

— ion exchange resins (U.S. Pat. No. 3,565,885);
— alkali metal and alkaline earth metal alcoholates, particularly aluminum alcoholates (EP 0132046);
— salts of weak acids and strong bases, such as sodium carbonate or sodium acetate (U.S. Pat. No. 4,939,245).

All the solutions proposed hitherto do indeed make it possible to improve the coloration of the finished products.

Nevertheless these solutions prove inadequate when it is desired to obtain very weakly colored products.

It is for this reason that it has been proposed also to resort to more or less complex decolorization and/or color stabilization processes:

— treatment with ozone (DE 3910269 and WO 91/090043);
— color stabilization with sodium metabisulphite (U.S. Pat. No. 4,557,729);
— decolorization by using active charcoals (EP 306 650).

Processes for limiting the formation of colored products, by removal of the residual sugars from the reaction medium upstream, have also been proposed:

— catalytic hydrogenation (U.S. Pat. No. 4,904,774);
— treatment with sodium borohydride (EP 387 916 and EP 388 857).

SUMMARY OF THE INVENTION

One object of the present invention is to solve the technical problem which consists in providing a novel process for the preparation of alkylpolyosides which yields very weakly colored or colorless products containing a reduced amount of acid degradation products, without resorting to complementary processes for the removal of residual sugars, decolorization and/or color stabilization.

A further object of the present invention is to provide a novel process which satisfies the aforesaid requirements and can be carried out easily and inexpensively on the industrial scale.

The solution to this technical problem, according to the present invention, consists of a process for the preparation of an alkylpolyoside containing from 6 to 32 carbon atoms in its alkyl chain, of the type comprising:

a) the reaction, in the presence of an acid catalyst, of a monosaccharide or a source of monosaccharide with — either a fatty alcohol having a hydrocarbon chain containing at least 6 carbon atoms,
— or a lower alcohol of the formula $C_nH_{2n+1}OH$, in which n is an integer between 1 and 5, and a fatty alcohol having a hydrocarbon chain containing at least 6 carbon atoms;

b) the neutralization of the catalyst used in step a); and
c) the removal of the excess fatty alcohol; characterized in that the neutralizing agent used in step b) above is a tertiary amine of the formulae

or

-continued

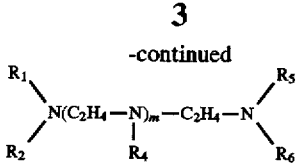

in which:

—m is an integer between 0 and 5; and

—$R_1$, $R_2$, $R_3$, $R_4$, $R_5$ and $R_6$, which are identical or different, are independently:

an alkyl radical having from 1 to 6 carbon atoms, a hydroxyalkyl or dihydroxyalkyl radical having from 2 to 4 carbon atoms, a phenyl radical, or a radical of the formula $(C_nH_{2n}-O)_xH$, in which n is an integer between 2 and 4 and x is an integer between 2 and 5, —it being possible for $R_1R_2$, taken together with the nitrogen atom to which they are attached, to be a saturated or unsaturated, substituted or unsubstituted heterocycle having from 5 to 7 ring members and containing from 1 to 3 heteroatoms selected from oxygen, nitrogen and sulfur.

DETAILED DESCRIPTION OF THE INVENTION

The present invention is actually based on the surprising and unexpected discovery that the use of tertiary amine bases of formulae (IA) and (IB), as defined above, in the neutralization of the etherification catalysts affords a considerable improvement in the quality of the alkylpolyosides obtained, especially as regards the coloration and the content of acid degradation products.

These tertiary amine bases are inert towards the reducing sugars used, and the absence of a hydrogen atom on the nitrogen eliminates the possibility of a secondary reaction generating colored by-products.

Moreover, the presence of a lone pair on the nitrogen atom makes it possible to neutralize the medium by forming a quaternary ammonium derivative and leads to much more stable pH values than with the mineral or organic bases used hitherto, both during the actual neutralization step itself and during the fatty alcohol distillation phase.

Finally, because of a better compatibility with the reaction medium, the pH adjustment is greatly facilitated so its optimization during the distillation becomes much less critical than with the neutralizing agents used hitherto. The acidity of the products obtained is also appreciably lower.

The preferred compounds of formulae IA according to the invention are those in which at least one of $R_1$, $R_2$ and $R_3$ is a hydroxyalkyl or dihydroxyalkyl radical having from 2 to 4 carbon atoms.

The most advantageous of these preferred compounds are selected from triethanolamine, triisopropanolamine, N-methyldiethanolamine, N,N-dimethylethanolamine, N,N-dimethylpropanolamine, N,N-diethyldihydroxypropylamine and N,N-dibutylethanolamine.

Another preferred class of compounds of formula IA according to the invention comprises the compounds in which $R_1R_2$, taken together with the nitrogen atom to which they are attached, form a heterocycle and $R_3$ is an alkyl radical having from 1 to 6 carbon atoms or a hydroxyalkyl radical having from 2 to 4 carbon atoms.

N-Methylpyrrole, N-methylpyrrolidone, N-methylpyrrolidine, N-methylpiperidine, N-methylmorpholine and N-hydroxyethylmorpholine may be mentioned among these preferred nitrogen heterocycles.

The preferred compounds of formula IB according to the invention are those in which m is equal to 0 and at least one of $R_1$, $R_2$, $R_5$ and $R_6$ is a hydroxyalkyl radical having from 2 to 4 carbon atoms.

N,N,N',N'-Tetrakis(hydroxypropyl)ethylenediamine may be mentioned among these preferred compounds.

It should be noted that all the abovementioned compounds have the advantage of being perfectly well known and present no problems from the toxicological point of view since they are commonly employed particularly in body hygiene products.

Thus such compounds can be used without appreciable problems and do not have to be removed from the finished products.

This applies for example to triethanolamine or N,N,N', N'-tetrakis(hydroxypropyl)ethylenediamine.

In the process according to the present invention, steps a and c are conventional and those skilled in the art may refer to the literature, and especially to the numerous documents cited above, in order to determine the most appropriate reaction conditions.

The fatty alcohol used in step a) can be represented by the formula $R(OR')_yOH$, in which R is a straight-chain or branched-chain alkyl, alkenyl or alkylphenyl radical having from 6 to 22 carbon atoms, R' is an alkylene group having from 2 to 4 carbon atoms and y is a number between 0 and 20.

The alcohols which can be used include linear or branched alcohols such as hexanol, heptanol, octanol, nonanol, decanol, dodecanol, tridecanol, tetradecanol, pentadecanol, hexadecanol, heptadecanol, octadecanol, methylpentanol, methylhexanol, methylheptanol, methyloctanol, methylnonanol, methyldecanol, methylundecanol, methyltridecanol, methyltetradecanol, methylpentadecanol, methylpentadecanol, methylhexadecanol, methylheptadecanol, ethylhexanol, ethyloctanol, ethyldecanol, ethyldodecanol, heptan-2-ol, nonan-2-ol, undecan-2-ol, tridecan-2-ol, pentadecan-2-ol, heptadecan-2-ol, 2-butyloctanol, 2-hexyloctanol, 2-octyloctanol, 2-hexyldecanol and 2-octyldecanol, alkenols such as hexenol, heptenol, octenol, nonenol, decenol, undecenol, dodecenol, tridecenol, tetradecenol, pentadecenol, hexadecenol, heptadecenol, heptadecenol and octadecenol, alkylphenols such as octylphenol and nonylphenol, and aryl alcohols such as, for example, benzyl alcohol.

These alcohols or their alkoxylated adducts can be used by themselves or in a mixture.

The saccharides used in the process according to the present invention are monosaccharides, disaccharides, oligosaccharides or polysaccharides.

Glucose, mannose, galactose, allose, altrose, gulose or dextrose, idose, talose, arabinose, ribose, xylose and lyxose may be mentioned among the monosaccharides which can be used, glucose being particularly preferred for reasons of availability and low cost.

Maltose, maltotriose, lactose, sucrose, gentobiose and cellobiose may be mentioned among the disaccharides and oligosaccharides which can be used.

Cellulose, starch, amylopectin, hemicellulose, inulin, dextrone, dextrin, xylan and glucose syrups may be mentioned among the polysaccharides which can be used.

The amount of alcohol and saccharide used in step a will generally be such that the molar ratio of alcohol to ose monomer is 1:1 to 8:1.

The acid catalyst used in step a can be selected from those generally known in the art, particularly sulfuric acid, paratoluenesulfonic acid, hydrochloric acid, phosphoric acid, phosphorous acid, hypophosphorous acid and mixtures thereof.

The amount of acid catalyst used will be about 0.001 to 0.05 mmol per mmol of ose monomer.

In step a the reaction temperature will generally be between about 90° and about 120° C. and the reaction time will generally be between about 3 and about 6 hours.

The amount of neutralizing agent used in step b) of the process of the present invention must be sufficient to enable a pH of between 5 and 9 to be obtained.

The neutralizing agent can be added to the reaction mixture in the form of a powder or in the form of a solution or dispersion in a solvent.

After neutralization of the acid catalyst, it is desirable to remove the excess alcohol by distillation. This can be done in conventional manner, for example in a film evaporator at a temperature of 170° to 200° C. under a residual pressure of 1 to 10 mm of mercury.

The invention will be illustrated by the non-limiting Examples below, which are given solely by way of illustration.

All the percentages in these Examples are expressed by weight, unless indicated otherwise.

EXAMPLE 1 TO 6

48 kg of fatty alcohol having a molecular weight of about 165 and the following average composition:

$C_{10}H_{21}OH$: 85%

$C_{12}H_{25}OH$: 12%

$C_{14}H_{29}OH$: 3% are introduced into a multipurpose reactor with a capacity of 120 liters, equipped with a condenser and a round-bottomed receiver.

After the addition of 13.1 kg of anhydrous glucose, the temperature of the mixture is raised to 90° C., with continuous stirring.

The acid catalyst, consisting of a mixture comprising 0.095 kg of 98% sulfuric acid and 0.065 kg of 50% hypophosphorous acid, is then introduced into the reactor.

The reaction mixture is heated to a temperature of 105° C. under a residual pressure of 15 mm of mercury in order to remove the water originating from the formation of the alkylpolyoside.

These temperature and pressure conditions are maintained for three hours and the degree of conversion of the glucose to alkylpolyoside reaches a value of 97%.

The medium is then cooled to 45° C.

The resulting reaction product is divided into several fractions for comparative neutralization tests.

The excess fatty alcohol in each of the fractions obtained after neutralization is removed by distillation on a film evaporator.

The alkylpolyoside obtained is taken up in water to give a solution with a solids content of about 55%.

Table 1 below collates the results obtained and mentions, for each Example, the nature of the neutralizing agent used, the pH of neutralization and the main characteristics of the reaction products obtained.

TABLE 1

| EXAMPLE | BASE USED | pH OF NEUTRALIZATION IN 1% DILUTION | FINISHED PRODUCT - pH OF PRODUCT VCS COLORATION SOLIDS CONTENT |
|---|---|---|---|
| 1 | TRIETHANOLAMINE | pH 1%: 8.3 | pH: 7.5 COLORATION: 5 SOLIDS CONTENT: 54.9% |
| 2 | TRIETHANOLAMINE | pH 1%: 7.5 | pH: 6.75 COLORATION: 5- SOLIDS CONTENT: 54.4% |
| 3 | N,N,N',N'-tetrakis-(hydroxypropyl)-ethylenediamine | pH 1%: 5.65 | pH: 5.25 COLORATION: 5+ SOLIDS CONTENT: 55.1% |
| 4 | SODIUM HYDROXIDE | pH 1%: 7.95 | pH: 5.0 COLORATION: 15 SOLIDS CONTENT: 54.6% |
| 5 | DIETHYLENE-GLYCOLAMINE | pH 1%: 8.8 | pH: 2.9 COLORATION: 17 SOLIDS CONTENT: 55.0% |
| 6 | SODIUM ACETATE | pH 1%: 5.55 | pH: 7.0 COLORATION: 18 SOLIDS CONTENT: 55.0% |

EXAMPLES 7 TO 9

An analogous test was carried out by repeating the above-described experimental protocol up to the neutralization stage and using 0.111 kg of sulfuric acid as the acid catalyst for 15.35 kg of anhydrous glucose amd 56.30 kg of fatty alcohol.

After a reaction time of three hours, the degree of conversion of the glucose reaches 96%.

The medium is then cooled to 45° C.

The resulting reaction product is divided into several fractions for comparative neutralization tests.

The excess fatty alcohol in each of the fractions obtained after neutralization is removed by distillation on a film evaporator.

The alkylpolyoside obtained is taken up in water to give a solution with a solids content of about 55%.

Table 2 below collates the results obtained and mentions, for each Example, the nature of the neutralizing agent used, the pH of neutralization and the main characteristics of the reaction products obtained.

TABLE 2

| EXAMPLE | BASE USED | pH OF NEUTRALIZATION IN 1% DILUTION | FINISHED PRODUCT - pH OF PRODUCT VCS COLORATION SOLIDS CONTENT |
|---|---|---|---|
| 7 | TRIETHANOLAMINE | pH 1%: 5.70 | pH: 6.25 COLORATION: 4 SOLIDS CONTENT: 57.3% |
| 8 | N,N,N',N'-tetrakis-(hydroxypropyl)-ethylenediamine | pH 1%: 5.25 | pH: 4.70 COLORATION: 5- SOLIDS CONTENT: 56.2% |

TABLE 2-continued

| EXAMPLE | BASE USED | pH OF NEUTRAL-IZATION IN 1% DILUTION | FINISHED PRODUCT - pH OF PRODUCT VCS COLORATION SOLIDS CONTENT |
|---|---|---|---|
| 9 | SODIUM HYDROXIDE | pH 1%: 5.35 | pH: 2.60 COLORATION: 4 SOLIDS CONTENT: 57.5% |

The Comparative Examples given above clearly show that the use of the tertiary amines of formula IA and IB in the neutralization of the etherification catalysts affords a considerable improvement in the quality of the alkylpolyosides obtained in terms of coloration and limitation of the formation of acid degradation products (stability of the pH during distillation), especially compared with the neutralizing agents in normal use, such as sodium hydroxide, sodium acetate or primary amines like diethyleneglycolamine.

EXAMPLE 10

A test analogous to those performed above was carried out up to the neutralization stage using 0.026 kg of chlorosulfonic acid ($ClSO_3H$) for 3.12 kg of anhydrous glucose and 11.44 kg of fatty alcohol.

After a reaction time of 3 hours, the degree of conversion of the glucose reaches 96%.

The reaction medium, cooled to 45° C., is neutralized with triethanolamine, the resulting pH of neutralization, measured in 1% dilution, being 6.60.

After distillation and dissolution effected as in the previous tests, the product obtained has the following physicochemical characteristics:

—pH of product 6.10
—VCS coloration 3
—Solids content 55.4%

What is claimed is:

1. A process for the preparation of an alkylpolyoside containing from 6 to 32 carbon atoms in its alkyl chain, comprising the steps of:

a) reacting, in the presence of an acid catalyst, a saccharide or a source of saccharide with
      either a fatty alcohol having a hydrocarbon chain containing at least 6 carbon atoms,
      or a lower alcohol of the formula $C_nH_{2n+1}OH$, in which n is an integer between 1 and 5, and a fatty alcohol having a hydrocarbon chain containing at least 6 carbon atoms;

b) neutralizing the catalyst used in step a); and c) removing excess fatty alcohol, wherein the neutralizing takes place using a neutralizing agent which is a tertiary amine of the formulae $$R_1-N\begin{array}{c}R_2\\R_3\end{array} \quad (IA)$$

or $$R_1\diagdown N(C_2H_4-N)_m-C_2H_4-N\diagup R_5 \quad (IB)$$
$$R_2\diagup \qquad\qquad\qquad\qquad\qquad \diagdown R_6$$

in which:

m is an integer between 0 and 5; and $R_1$, $R_2$, $R_3$, $R_4$, $R_5$ and $R_6$, which are identical or different, are independently:

an alkyl radical having from 1 to 6 carbon atoms, a hydroxyalkyl or dihydroxyalkyl radical having from 2 to 4 carbon atoms, a phenyl radical, or a radical of the formula $(C_nH_{2n}-O)_xH$, in which n is an integer between 2 and 4 and x is an integer between 2 and 5, and wherein $R_1R_2$ may be taken together with the nitrogen atom to which they are attached to be a saturated or unsaturated, substituted or unsubstituted heterocycle having from 5 to 7 ring members and containing from 1 to 3 heteroatoms selected from the group consisting of oxygen, nitrogen and sulfur.

2. A process according to claim 1 wherein said neutralizing agent is a tertiary amine of formula IA in which at least one of $R_1$, $R_2$ and $R_3$ is a hydroxyalkyl or dihydroxyalkyl radical having from 2 to 4 carbon atoms.

3. A process according to claim 2 characterized in neutralizing agent is triethanolamine.

4. A process according to claim 1 wherein said neutralizing agent is a heterocyclic tertiary amine of formula IA in which $R_1R_2$, taken together with the nitrogen atom to which they are attached, form a heterocycle selected from the group consisting of pyrrole, pyrrolidone, pyrrolidine, piperidine and morpholine, and $R_3$ is an alkyl radical having from 1 to 6 carbon atoms or a hydroxyalkyl radical having from 2 to 4 carbon atoms.

5. A process according to claim 4 wherein said neutralizing agent is selected from the group consisting of N-methylpyrrole, N-methylpyrrolidone, N-methylpyrrolidine, N-methylpiperidine, N-methylmorpholine and N-hydroxyethylmorpholine.

6. A process according to claim 1 wherein said neutralizing agent is a tertiary amine of formula IB in which:

—m is equal to 0 and

—at least one of $R_1$, $R_2$, $R_5$ and $R_6$ is a hydroxyalkyl radical having from 2 to 4 carbon atoms.

7. A process according to claim 6 wherein said neutralizing agent is N N N',N'-tetrakis(hydroxypropyl) ethylenediamine.

8. A process according to claim 1 wherein said neutralizing agent is used in an amount sufficient to enable a pH of between 5 and 9 to be obtained.

* * * * *